United States Patent
Noguchi

(10) Patent No.: US 7,916,840 B2
(45) Date of Patent: Mar. 29, 2011

(54) RADIATION DIAPHRAGM APPARATUS AND RADIOTHERAPY APPARATUS HAVING THE DIAPHRAGM APPARATUS

(75) Inventor: Tadashi Noguchi, Otawara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 11/365,519

(22) Filed: Mar. 2, 2006

(65) Prior Publication Data

US 2006/0198492 A1 Sep. 7, 2006

(30) Foreign Application Priority Data

Mar. 4, 2005 (JP) ................................. 2005-061599
Jan. 31, 2006 (JP) ................................. 2006-023577

(51) Int. Cl.
*G21K 1/04* (2006.01)
*G21K 1/02* (2006.01)
(52) U.S. Cl. ................ 378/150; 378/147; 378/149
(58) Field of Classification Search ............... 378/65, 378/147–153, 144; 384/7, 26, 50, 91, 125, 384/275, 445; 403/243, 351, 365; 464/68.6, 464/92, 132, 160–162, 178; 16/2.1, 2.5; 295/35
See application file for complete search history.

(56) References Cited

U.S. PATENT DOCUMENTS

| | | | | |
|---|---|---|---|---|
| 2,858,450 A | * | 10/1958 | Holben | 250/498.1 |
| 4,357,555 A | * | 11/1982 | Gerkema et al. | 378/135 |
| 4,672,212 A | * | 6/1987 | Brahme | 250/505.1 |
| 4,715,056 A | * | 12/1987 | Vlasbloem et al. | 378/152 |
| 4,794,629 A | * | 12/1988 | Pastyr et al. | 378/152 |
| 4,868,844 A | * | 9/1989 | Nunan | 378/152 |
| 5,713,808 A | * | 2/1998 | Ohta | 474/94 |
| 5,860,218 A | * | 1/1999 | Vinciguerra | 30/392 |
| 6,041,100 A | * | 3/2000 | Miller et al. | 378/141 |
| 6,052,436 A | * | 4/2000 | Huttner et al. | 378/152 |

(Continued)

FOREIGN PATENT DOCUMENTS

JP 62-277972 12/1987

(Continued)

OTHER PUBLICATIONS

Japanese Office Action issued Oct. 26, 2010, in Japan Patent Application No. 2006-023577 (with English translation).

*Primary Examiner* — Edward J Glick
*Assistant Examiner* — Anastasia Midkiff
(74) *Attorney, Agent, or Firm* — Oblon, Spivak, McClelland, Maier & Neustadt, L.L.P.

(57) ABSTRACT

A radiation diaphragm apparatus, which is adapted to form a radiation field, which is an exposed area of an object to be examined by radiation from a radiation source, comprises a plurality of diaphragm elements which are closely arranged in a first direction and movable along a second direction substantially normal to the first direction and each of which has a hole of a given shape formed to penetrate through it in the first direction, a shaft penetrating through the hole of each of the diaphragm elements, and a wear-resistant surface member coating the shaft. The shaft supports each of the diaphragm elements at a point of contact with the periphery of the hole. The diaphragm elements move along the second direction with support by the shaft.

12 Claims, 12 Drawing Sheets

U.S. PATENT DOCUMENTS

| | | | |
|---|---|---|---|
| 6,227,545 B1 * | 5/2001 | Kugler | 277/306 |
| 6,240,582 B1 * | 6/2001 | Reinke | 5/601 |
| 6,459,769 B1 * | 10/2002 | Cosman | 378/147 |
| 6,485,115 B1 * | 11/2002 | Egle | 305/199 |
| 7,020,245 B2 * | 3/2006 | Noguchi | 378/150 |
| 2004/0041462 A1 * | 3/2004 | Hicks | 301/105.1 |
| 2004/0240621 A1 * | 12/2004 | Noguchi | 378/150 |
| 2005/0185766 A1 * | 8/2005 | Tsujita | 378/150 |
| 2006/0067480 A1 * | 3/2006 | Juschka et al. | 378/150 |
| 2006/0096399 A1 * | 5/2006 | Harper et al. | 74/424.71 |

FOREIGN PATENT DOCUMENTS

| | | |
|---|---|---|
| JP | 1-146565 | 6/1989 |
| JP | 6-210012 | 8/1994 |
| JP | 11-216197 | 8/1999 |
| JP | 2001-66397 | 3/2001 |
| JP | 2002-210026 | 7/2002 |
| JP | 2002-224230 | 8/2002 |
| JP | 2002253686 A * | 9/2002 |
| JP | 2004-275243 | 10/2004 |
| JP | 2004275243 A * | 10/2004 |

* cited by examiner

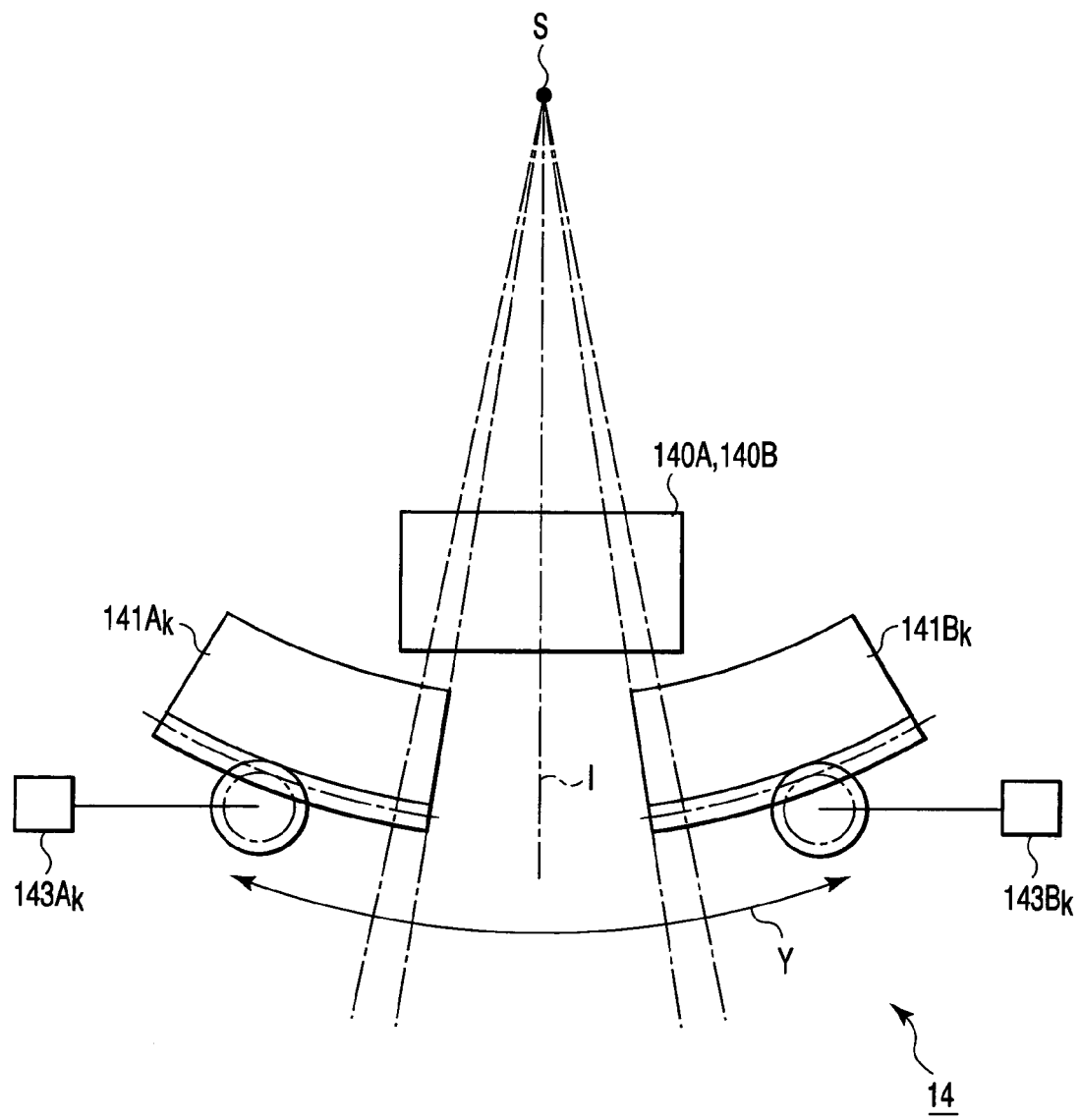
F I G. 2

RADIATION DIAPHRAGM APPARATUS AND RADIOTHERAPY APPARATUS HAVING THE DIAPHRAGM APPARATUS

CROSS-REFERENCE TO RELATED APPLICATIONS

This application is based upon and claims the benefit of priority from prior Japanese Patent Applications No. 2005-061599, filed Mar. 4, 2005; and No. 2006-023577, filed Jan. 31, 2006, the entire contents of both of which are incorporated herein by reference.

BACKGROUND OF THE INVENTION

1. Field of the Invention

The present invention relates to a radiation diaphragm (stop) apparatus for accurately forming a radiation field which is an area to be exposed to radiation for use in apparatus adapted for radiotherapy or radiation-based nondestructive inspection and a radiotherapy apparatus equipped with the radiation diaphragm apparatus.

2. Description of the Related Art

The radiotherapy apparatus is one which irradiates a given region containing a diseased part with ionizing radiation to destroy diseased tissues, thereby allowing treatment of the diseased part. Treatments using this apparatus include post-operation treatment, under-operation treatment, noninvasive treatment, etc. The purpose of the postoperation treatment is to, after a surgical operation has been performed on a patient to remove a malignant tumor in a diseased part, externally apply radiation to the diseased part to destroy the remaining tumor cells the operation has failed to remove. The purpose of the under-operation treatment is to directly apply radiation to unremoved tumor cells while the diseased part is cut open. The purpose of the noninvasive treatment is to apply radiation to a diseased part of a patient without opening the diseased part. Advances in computer technology and medical technology have allowed the recent radiotherapy apparatus to irradiate an object of treatment with radiation in large doses, but irradiate surrounding normal tissues with as little radiation as possible. Thus, the radiotherapy is receiving attention as a treatment that has few side effects and is little invasive (or noninvasive).

With such a radiotherapy apparatus, because of its property of irradiating a diseased part with radiation, provisions are made for reducing exposure of a patient to radiation. One of the provisions is to equip the apparatus with a split diaphragm apparatus for restricting the radiation field so that radiation is accurately applied to the diseased part (region for treatment) (see, for example, Japanese Unexamined Patent Publications Nos. 2004-275243 and 2002-210026).

FIG. 1 is a diagram for use in explanation of an example of a conventional split diaphragm apparatus. As shown, first diaphragm elements 100A and second diaphragm 100B are arranged along one direction (X-axis direction in the diagram). The first and second diaphragm elements are configured to be movable in the Y-axis direction normal to the X-axis direction (that is, the first and second diaphragm elements facing each other can be moved to approach each other or separate from each other). By moving each diaphragm element to a desired position, a radiation field of a desired shape can be formed.

Each diaphragm element is formed of a heavy metal, such as tungsten, which is capable of blocking radiation. Therefore, its weight is heavy and the supporting mechanism requires accommodations. The conventional supporting mechanisms include one which supports each diaphragm block with a grooved roller (see, for example, Japanese Unexamined Patent Publication No. 6-210012 and Japanese Patent Application No. 63-267324), one in which each diaphragm element is formed with grooves of V (U)-shaped cross section on both sides, balls and retainers are placed in the grooves, and springs are placed at both ends of each of the grooves to thereby allow adjacent diaphragm blocks to support each other (see, for example, Japanese Unexamined Patent Publication No. 2001-066397), etc.

However, with the conventional radiotherapy apparatus, there are the following problems.

First, with the method of supporting each diaphragm element with a grooved roller, rolling contact results in the radial direction while slide friction results in the thrust direction. As the result, there arises a possibility that reliable accuracy may drop with time due to abrasion. In addition, since the diaphragm block is made of a heavy metal such as tungsten, the grooved roller must be increased in diameter. Thus, the diaphragm apparatus will increase in size to project in the direction of a patient, which will intensify the patient's oppressive feeling. Moreover, it becomes difficult to secure space sufficient to accommodate a standard auxiliary apparatus, such as a block tray, between the radiation source and the patient as needed. Furthermore, when the diaphragm block is subdivided, three or more grooved rollers must be placed for each diaphragm block. Therefore, a large number of rollers must be placed, taking up much space. Further, assembly and adjustment also become difficult.

With the method of using grooves of V (U)-shaped cross section formed on both the sides of each diaphragm element, the structure requires a large number of parts and a large number of steps of assembly. Thus, the cost increases. In addition, because of rolling contact, the driving power is low and looseness is liable to occur.

BRIEF SUMMARY OF THE INVENTION

It is therefore an object of the present invention to provide a diaphragm apparatus which supports diaphragm elements smoothly and reliably and is small in size, highly reliable, and relatively inexpensive and a radiotherapy apparatus using the diaphragm apparatus.

According to an aspect of the present invention, there is provided a radiation diaphragm apparatus which is placed between a radiation source and an object to be examined and adapted to form a radiation field which is an exposed area of the object to be examined to radiation from the radiation source and which comprises: a plurality of diaphragm elements which are arranged in a first direction and movable along a second direction different from the first direction and each of which includes a hole of a predetermined shape formed to penetrate through it in the first direction; a support unit which includes a shaft penetrating through the hole of each of the diaphragm elements and a wear-resistant surface member coating the shaft and supports each of the diaphragm elements at a point of contact with the periphery of the hole; and a moving unit which moves each of the diaphragm elements along the second direction to form the radiation field.

According to another aspect of the present invention, there is provided a radiotherapy apparatus which comprises: a radiation source to irradiate an object to be examined with radiation; a radiation diaphragm unit placed between the radiation source and an object to be examined and adapted to form a radiation field which is an exposed area of the object to be examined to radiation from the radiation source, which comprises a plurality of diaphragm elements which are arranged in a first direction and movable along a second direction different from the first direction and each of which includes a hole of a predetermined shape formed to penetrate through it in the first direction, and a support unit which includes a shaft penetrating through the hole of each of the diaphragm elements and a wear-resistant surface member coating the shaft and supports each of the diaphragm elements at a point of contact with the periphery of the hole; a moving unit which moves each of the diaphragm elements along the second direction to form the radiation field; and a control unit which controls the moving unit.

BRIEF DESCRIPTION OF THE SEVERAL VIEWS OF THE DRAWING

FIG. 2 is a side view of a diaphragm unit according to a first embodiment of the present invention;

DETAILED DESCRIPTION OF THE INVENTION

Figure 1A:
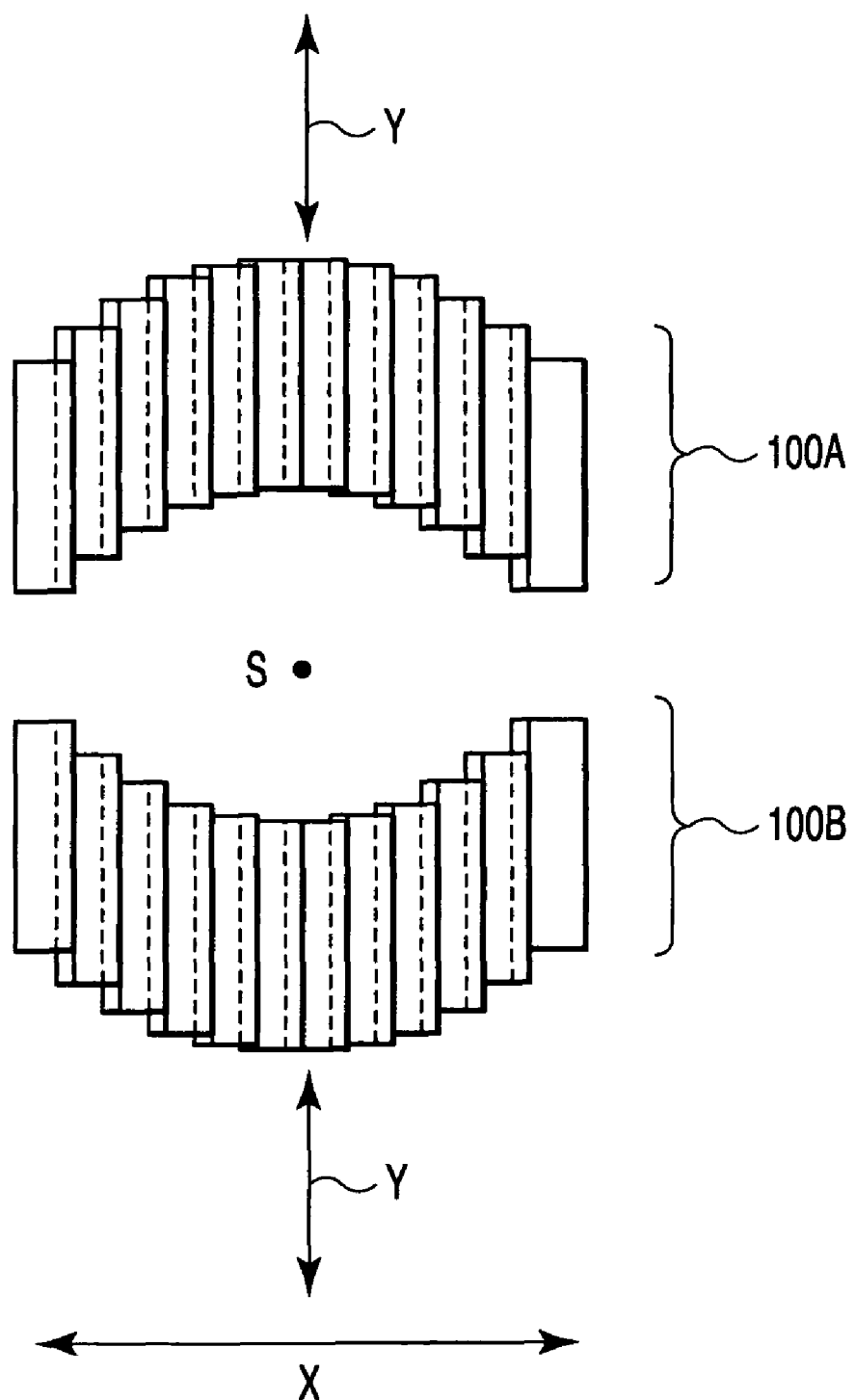
FIG. 1A is a diagram for use in explanation of an example of a conventional split diaphragm apparatus.

The preferred embodiments of the present invention will be described hereinafter with reference to the accompanying drawings. In the description, the same or functionally equivalent elements are denoted by the same or similar reference numerals, to thereby simplify the description.

Figure 1B:
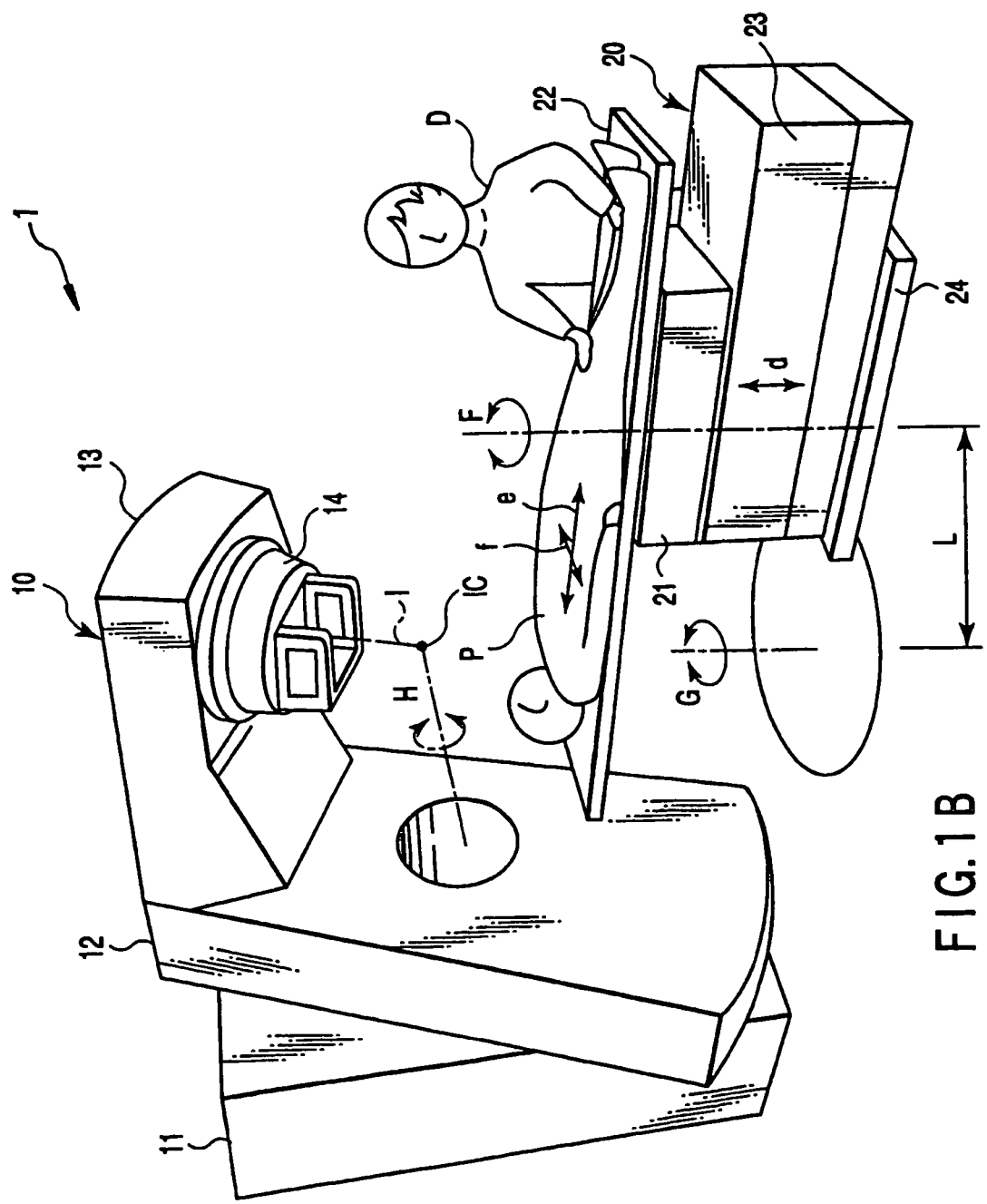
FIG. 1B is a schematic exterior view of a radiotherapy apparatus to which the present invention is applied.

FIG. 1B is a schematic exterior view of a radiotherapy apparatus 1 to which the present invention is adapted. As shown, the radiotherapy apparatus 1 includes a radiation irradiation apparatus 10 which irradiates an object to be examined with radiation from a radiation source, a treatment couch 20 on which the object to be examined P is laid down to locate an irradiation region, and a controller (not shown) which systematically controls the components of the radiotherapy apparatus including the radiation irradiation apparatus 10 and the treatment couch 20.

The radiation irradiation apparatus 10 includes a fixed frame, a rotating frame 12, an irradiation head 13, and a diaphragm unit 14. The fixed frame 11 is placed on the floor and the rotating frame 12 is rotatably mounted to the fixed frame. The irradiation head 13 is provided in the tip extending perpendicularly to the surface of the rotating frame 12 and equipped with the diaphragm unit 14 for shaping a radiation beam and determining a radiation field. The configuration of the diaphragm unit 14 will be described in detail later.

The rotating frame 12 is adapted to be rotatable about the axis H over nearly 360 degrees. The diaphragm unit 14 is also rotatable about the irradiation axis I of radiation emitted from the irradiation head 13. The intersection of the rotation axis H of the rotating frame 12 and the irradiation axis I is referred to as the isocenter IC. The rotating frame 12 is constructed to allow not only fixed irradiation of radiation but also other forms of irradiation, such as rotating irradiation, swing irradiation, intermittent irradiation, etc.

The treatment couch 20 is equipped with an upper structure 21, a top board 22, a lifting structure 23, and a lower structure 24 and is placed on the floor to be rotatable over a given range of angles in the direction of arrow G along a circle with center at the isocenter IC. The top board 22, which is a bed on which the object to be examined P under examination is laid down, is supported by the upper structure 21. The upper structure 21 is equipped with mechanisms to move the top board 22 in the forward and backward direction indicated by arrow e and in the right and left direction indicated by arrow f. The upper structure 21 is supported by the lifting structure 23. The lifting structure, which is constructed from, for example, a link mechanism, lifts the upper structure 21 and the top board 22 over a given range by being lifted itself in the up and down direction indicated by arrow d. The lifting structure 23 is supported by the lower structure 24. The lower structure is equipped with a mechanism to rotate the lifting structure 23 in the direction indicated by arrow F with center at the position at a distance L from the isocenter IC. Thereby, the upper structure 21 and the top board 22 can be rotated together with the lifting structure 23 through a given angle in the direction of arrow F.

In treatment, the positioning of the object to be examined P under examination and setting of the radiation field using the diaphragm unit 14 are performed by a medical staff D such as a doctor.

[Diaphragm Unit]

The configuration of the diaphragm unit will be described in detail below. In carrying out radiotherapy, it is important not to damage normal tissues by applying radiation only to a body region subjected to treatment, such as a malignant tumor, with concentration. The diaphragm unit is adapted to control (restrict) the radiation field so as to irradiate normal tissues with as little radiation as possible and is built into the irradiation head 13 to be rotatable around the irradiation axis I.

The embodiment will be described in terms of a split diaphragm unit having multiple diaphragm members each in the shape of a circular arc as will be described below. However, the principles of the invention is also applicable to a split diaphragm unit having multiple diaphragm members each in the shape of a rectangle. The configuration of the diaphragm unit 14 will be described below with reference to FIGS. 2 through 5.

Figure 3:
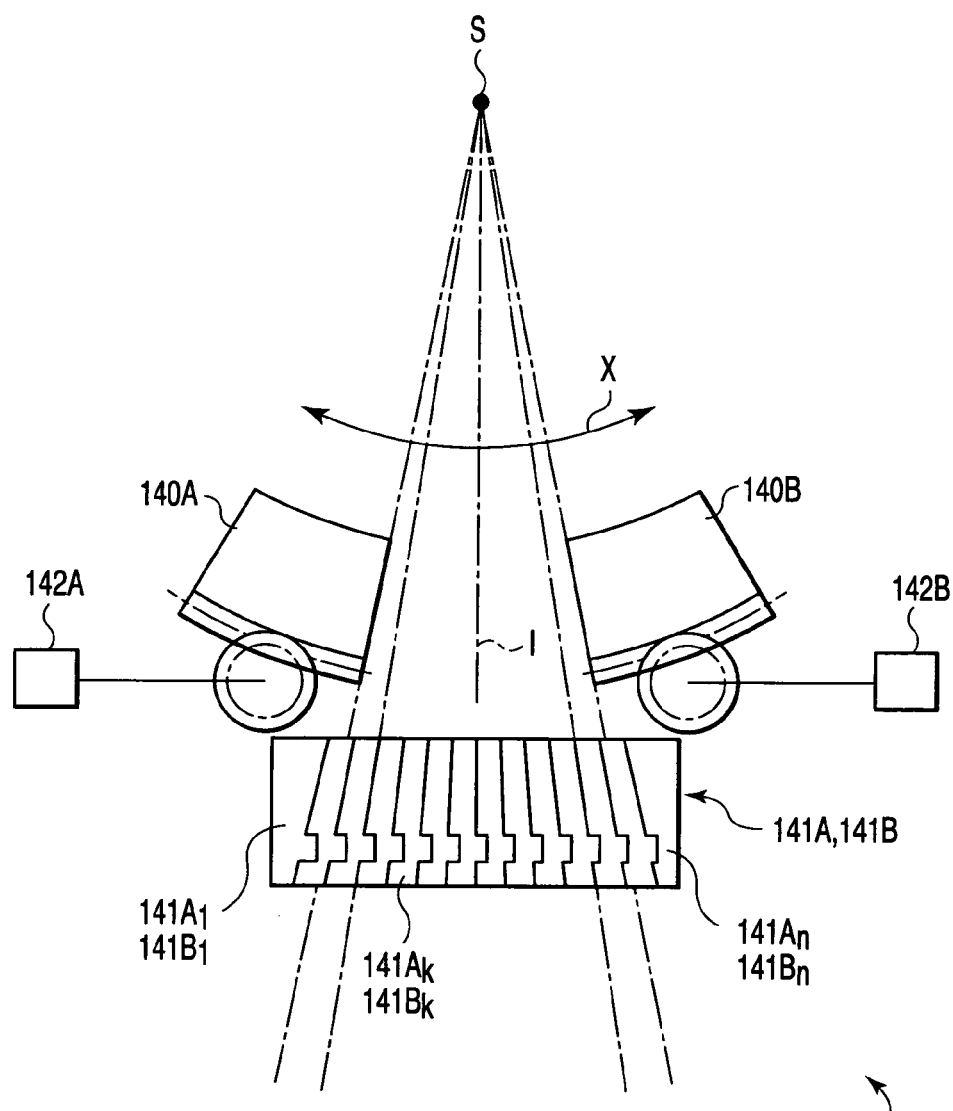
FIG. 3 is another side view of the diaphragm unit in a direction substantially normal to FIG. 2.

FIG. 2 is a side view of the diaphragm unit and FIG. 3 is another side view in a direction substantially normal to FIG. 2. In the practical radiotherapy apparatus 1, the diaphragm unit 14 is provided with a housing; however, it is omitted in FIGS. 2 and 3 for the sake of description.

The diaphragm unit 14 is equipped with first and second diaphragm members 140A and 140B, second diaphragm members 141Ak and 141Bk (k is a natural number in the range of 1 to n) each formed in the shape of a leaf, first drive units 142A and 142B, second drive units 143Ak and 143Bk (k is a natural in the range of 1 to n), and a supporting mechanism to be described later.

The first diaphragm members 140A and 140B are placed closer to the radiation source S than the second diaphragm members 141Ak and 141Bk and each consist of a single unit made from a heavy metal such as tungsten. The first diaphragm members 140A and 140B are placed so that their end surfaces face each other in a first direction (Y direction in FIG. 3) with the radiation irradiation axis I interposed therebetween. The first diaphragm members 140A and 140B are driven by the first drive units 142A and 142B, respectively, to move in the direction of arrow X along the orbital plane in the form of a circle with center at the radiation source S. That is, the first diaphragm members 140A and 140B are moved to approach each other or separate from each other.

The second diaphragm members 141Ak and 141Bk are placed more distant from the radiation source S than the first diaphragm members 140A and 140B and each consist of multiple diaphragm elements (split diaphragm element) made from a heavy metal of, say, tungsten. The second diaphragm members 141Ak and 141Bk are placed so that their end surfaces face each other in a second direction (X direction in FIG. 2) substantially normal to the first direction with the radiation irradiation axis I interposed therebetween. The second diaphragm members 141Ak and 141Bk are driven by the second drive units 143A and 143B, respectively, to move in the direction of arrow Y along the orbital plane in the form of a circle with center at the radiation source S. That is, the second diaphragm units 141Ak and 141Bk are moved to approach each other or separate from each other. The second drive member 141Ak is comprised of a number, n, of diaphragm elements 141A1 to 141An, which are densely arranged in the X direction so as to prevent the leakage of radiation therefrom. The same holds true for the second drive member 141Bk.

Figure 4:
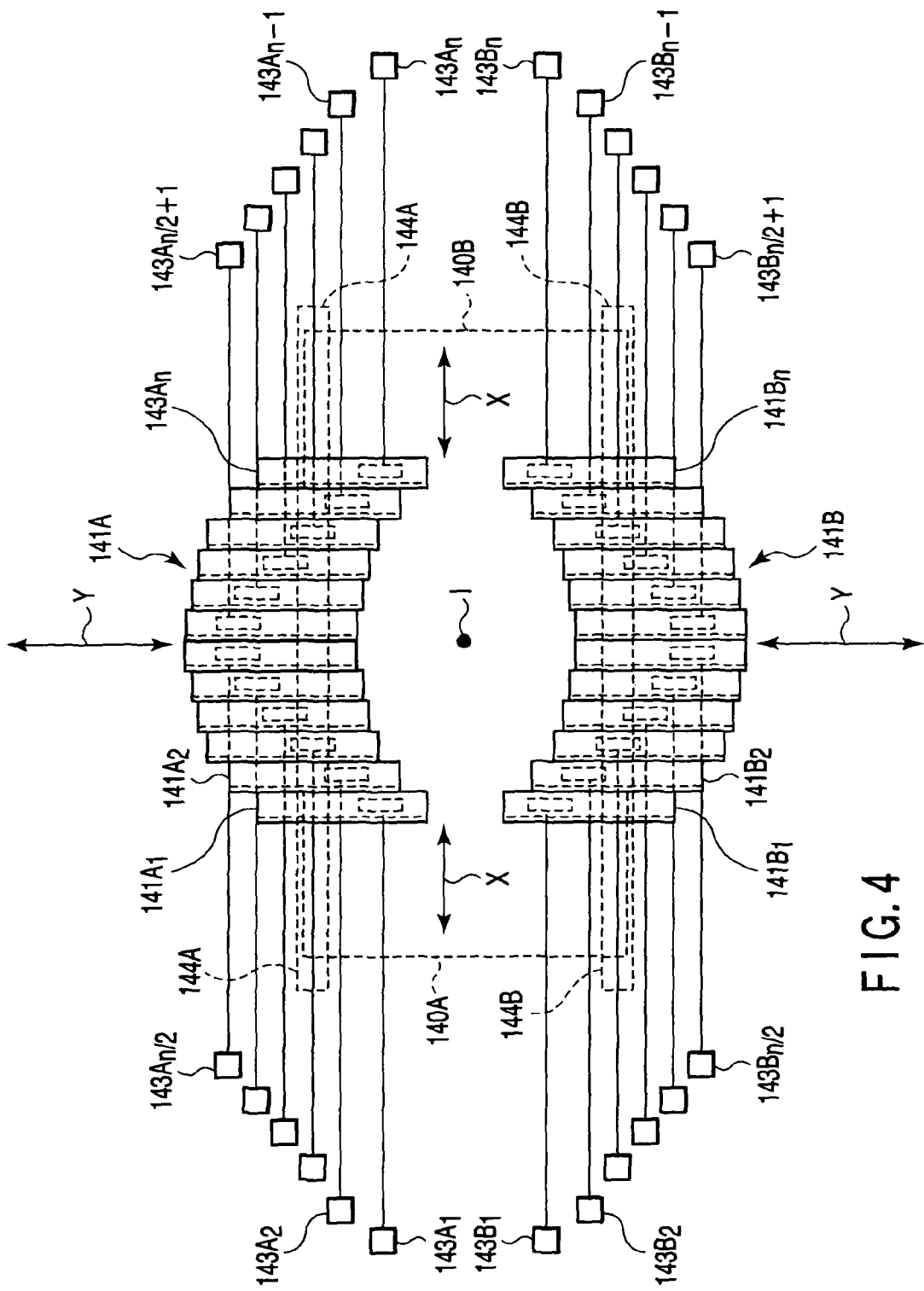
FIG. 4 is a view of the second diaphragm elements 141Ak and 141Bk and the second drive units 143Ak and 143Bk seen from the side of the radiation source S.

FIG. 4 is a view of the second diaphragm members 141Ak and 141Bk and the second drive units 143Ak and 143Bk seen from the side of the radiation source S. As shown, drive units 143A1 to 143An and 143B1 to 143Bn are provided for the second diaphragm elements 141A1 to 141An and 141B1 to 141Bn, respectively. Therefore, each of the diaphragm elements 141A1 to 141An and 141B1 to 141Bn is individually driven by a corresponding one of the drive units 143A1 to 143An and 143B1 to 143Bn to move in the direction of arrow Y along the orbital plane on a circle with center at the radiation source S. The corresponding second diaphragm elements 141Ak and 141Bk that face each other are driven to approach each other or separate from each other.

Figure 5:
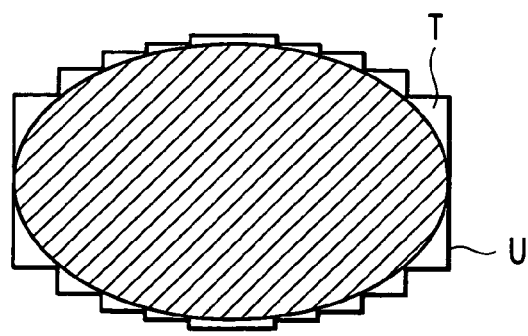
FIG. 5 shows an example of a radiation field U of an irregular shape made to approximate the shape of a body region to be treated.

Therefore, as shown in FIG. 5, a radiation field U of an irregular shape made to approximate the shape of a body region to be treated can be formed by moving each of the first diaphragm members 140A and 140B in the X direction and moving each of the second diaphragm elements 141Ak and 141Bk in the Y direction so that the corresponding diaphragm members or elements facing each other approach each other or separate from each other.

The diaphragm unit 14 is equipped with a supporting mechanism for supporting the second diaphragm members 141Ak and 141Bk smoothly and reliably.

Figure 6:
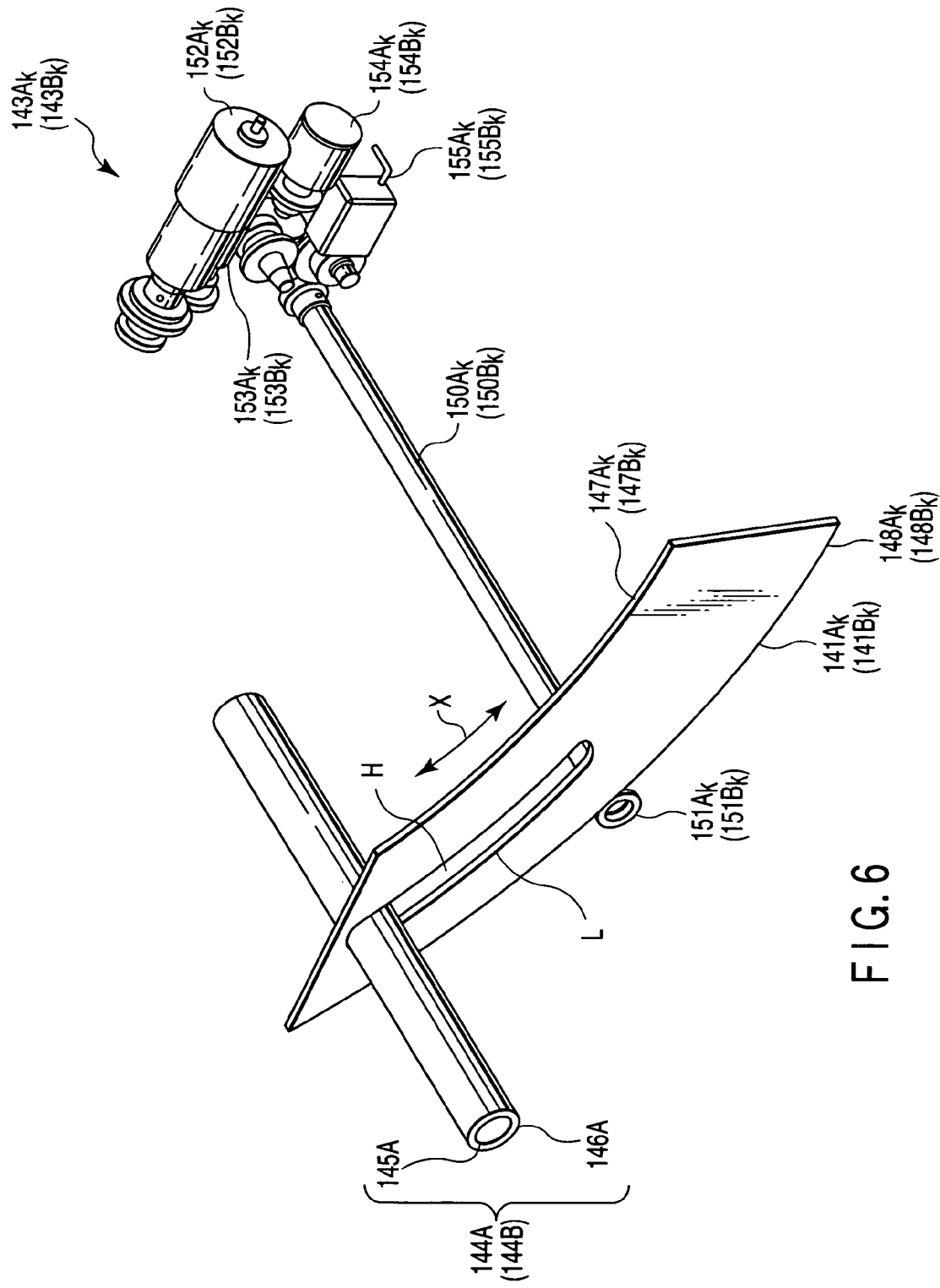
FIG. 6 is a diagram for use in explanation of a mechanism for supporting second diaphragm elements of the diaphragm unit of the embodiment.

FIG. 6 is a diagram for use in explanation of the supporting mechanism of the second diaphragm members 141Ak and 141Bk. As shown, each of the diaphragm elements 141Ak and 141Bk in the diaphragm unit 14 is formed with an orbital elongated hole L outside the useful beam (that is, outside the portion used to shield radiation). The elongated hole is formed along the X direction in the shape of a circular arc with center at the radiation source S.

The diaphragm unit 14 has a supporting member 144A which penetrates through each of the diaphragm elements 141Ak and a supporting member 144B which penetrates through each of the second diaphragm elements 141Bk. Each of the supporting members 144A and 144B is comprised of a shaft 145A (145B) and a surface member 146A (146B) which is a wear-resistant bush 146A (146B) and is provided outside the shaft. Note that, the surface member 146A (146B) is not limited to the wear-resistant bush. For example, a bearing, a collar material or the like may be used as the surface member 146A (146B).

The supporting member 144A (144B) contacts the second diaphragm element 141Ak (141Bk) in the peripheral portion of the hole L to support it. The inner edge 147A (147B) and the outer edge 148Ak (148Bk) are shaped into a convex form and supported by supporting members (not shown) made of a wear-resistant special alloy in the form of a comb provided outside the useful beam. Thus, the diaphragm element 141Ak (141Bk) has its load in the radial and thrust directions supported at three points by the supporting member 144A (144B) and the comb-shaped members into which the inner edge 147Ak (147Bk) and the outer edge 148Ak (148Bk) are fitted.

The wear-resistant bush 146A (146B) and the comb-shaped supporting members may be formed integrally or separately. The comb-shaped supporting members and the shaft 145A (145B) may be used for auxiliary purpose. The portions where the diaphragm element 141Ak (141Bk) is fitted into the comb-shaped supporting members, the inner edge 147Ak (147Bk) and the outer edge 148Ak (148Bk) may be formed with concave grooves. Rolling contact using balls may be used.

Next, the operation of moving the second diaphragm elements 141Ak and 141Bk will be described. The second diaphragm element 141Ak (141Bk) is formed with teeth on the outer edge. The teeth are engaged with a driving gear 151A (151Bk) of a drive unit 143Ak (143Bk) through a shaft 150Ak (150Bk) as shown in FIG. 5. The driving gear 151A (151Bk) is driven by a motor 152Ak (152Bk) as a driving source through a driving force transmission mechanism such as a worm gear 153Ak (153Bk). To detect the amount of driving, a potentiometer 154Ak (154Bk) and an encoder 155Ak (155Bk) are provided, which function as a detector for detecting the position of the diaphragm element 141Ak (141Bk). Thus, the motor 152Ak (152Bk) is controlled by the controller in the radiotherapy apparatus 1 on the basis of information from the potentiometer (154Ak (154Bk) and the encoder 155Ak (155Bk), thereby allowing the diaphragm element 141Ak (141Bk) to be set in a desired position.

The surface member 146A (146B) is coated on top with a wear-resistant material. Thus, when the second diaphragm element 141Ak (141Bk) is moved, abrasion infrequently occurs and stable accuracy can be maintained over a long period of time. Moderate resistance resulting from slide contact allows looseness (backlash) of the diaphragm element 141Ak (141Bk) to be minimized.

The surface member 146A (146B) is set to penetrate through the elongated hole L of the diaphragm element 141Ak (141Bk). Therefore, both the ends in the direction of length of the elongated hole L serve as mechanical limits in the directions to open or close the diaphragm. As the result, the diaphragm element 141Ak (141Bk) is not required to have any additional form adapted for mechanical limits, allowing the form of the diaphragm element to be simplified and the count of parts to be reduced.

Figure 7A:
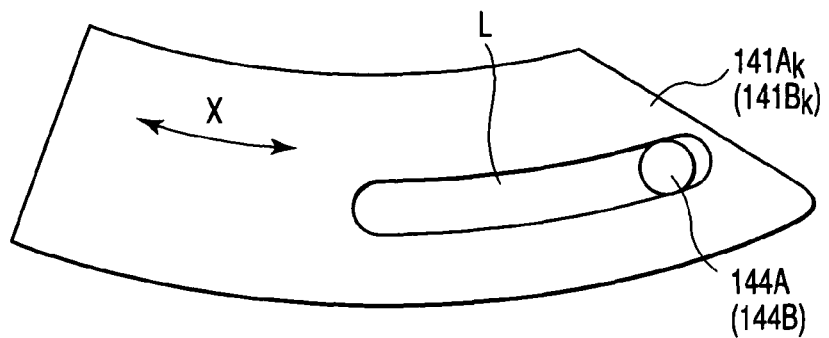
FIG. 7A is a diagram for use in explanation of the shape of an elongated hole formed in the second diaphragm element shaped into a circular arc.
Figure 7B:
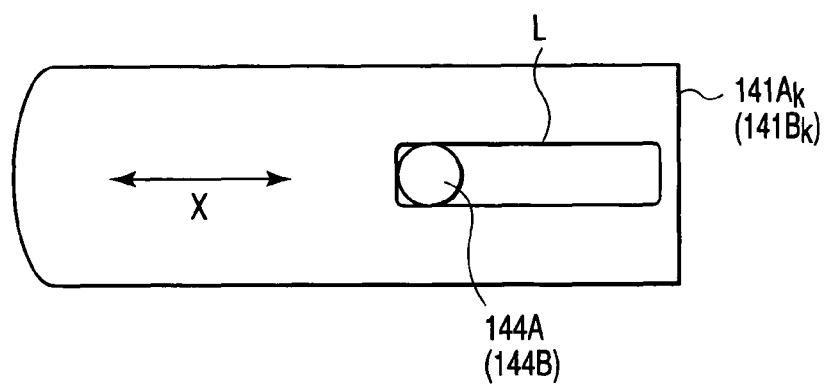
FIG. 7B is a diagram for use in explanation of the shape of an elongated hole formed in the second diaphragm element shaped into a rectangle.
Figure 8A:
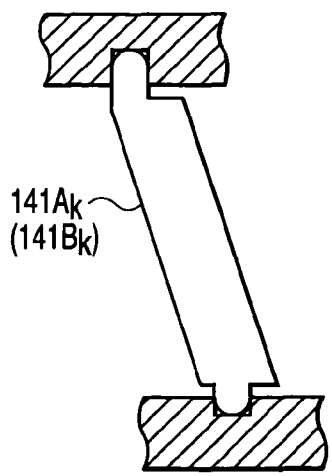
FIGS. 8A and 8B are diagrams for use in explanation of the forms of portions where the second diaphragm element is fitted into peripheral supporting members.
Figure 8B:
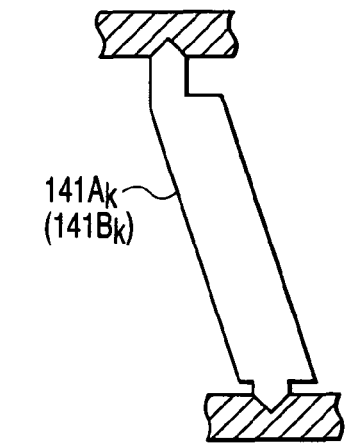

In the split diaphragm unit described above, the diaphragm elements 141Ak and 141Bk are formed in the shape of such a circular arc as shown in FIG. 6. Therefore, the shape of the elongated hole L is made to correspond to the circular-arc shape (or the locus of movement) of the second diaphragm element 141Ak (141Bk). In contrast, with a split diaphragm unit having multiple diaphragm elements each of a polyhedron (a rectangular form in FIG. 7) having a surface substantially normal to the radiation axis as shown in FIG. 7, the elongated hole L will have a rectangular shape. Irrespective of the shape of the diaphragm element 141Ak (141Bk), the portion where the diaphragm element 141Ak (141Bk) is fitted into the comb-shaped supporting member may be formed into a V- or U-shape as shown in FIGS. 8A and 8B. As an auxiliary, small rollers may be placed at regularly spaced intervals on the inner and outer edges 147Ak (147Bk) along the X-direction and 148Ak (148Bk) of the diaphragm element 141Ak (141Bk) to support it in combination with ball mechanism.

Figure 9:
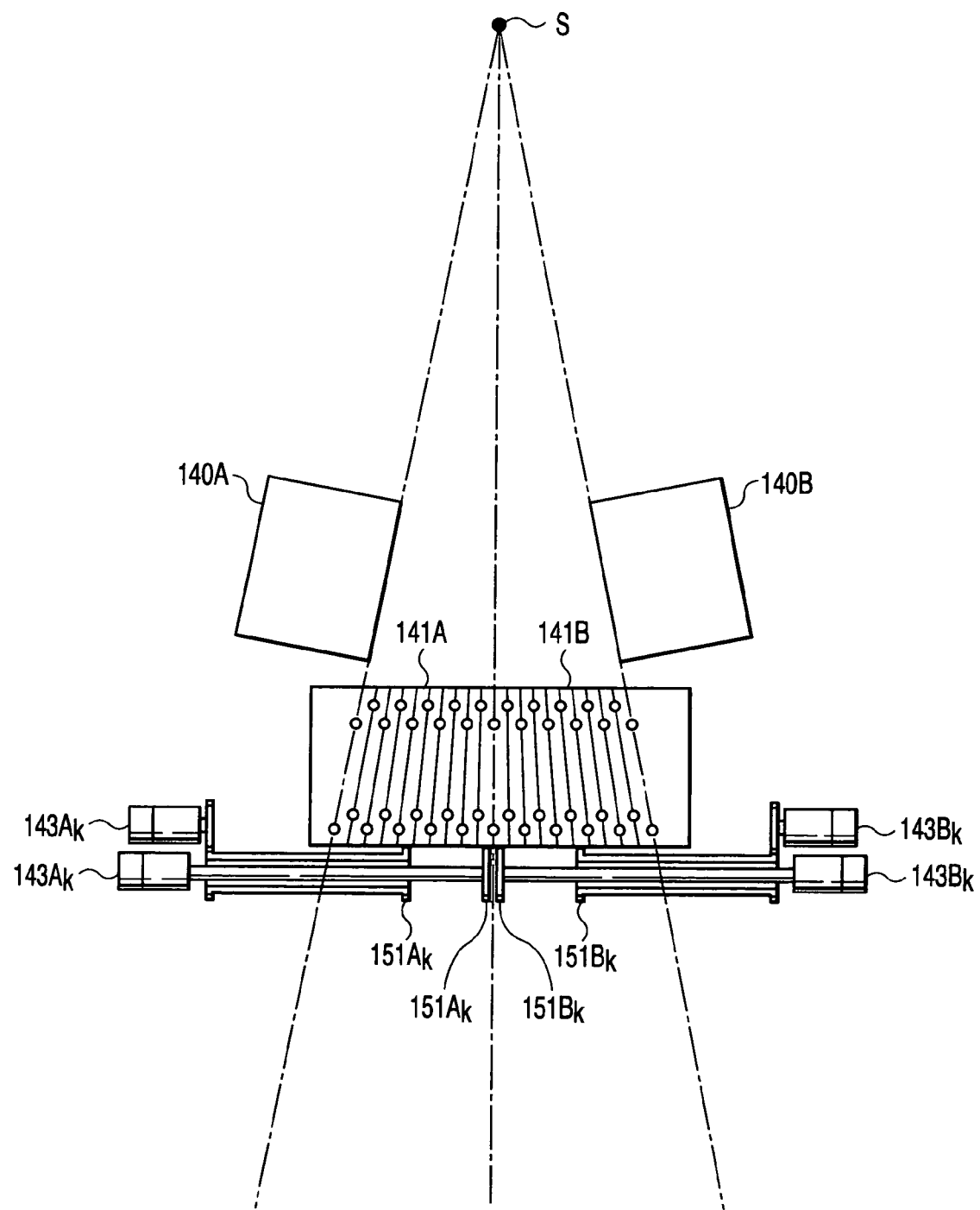
FIG. 9 is a diagram for use in explanation of an example of a diaphragm unit when the diaphragm elements are subdivided.
Figure 10:
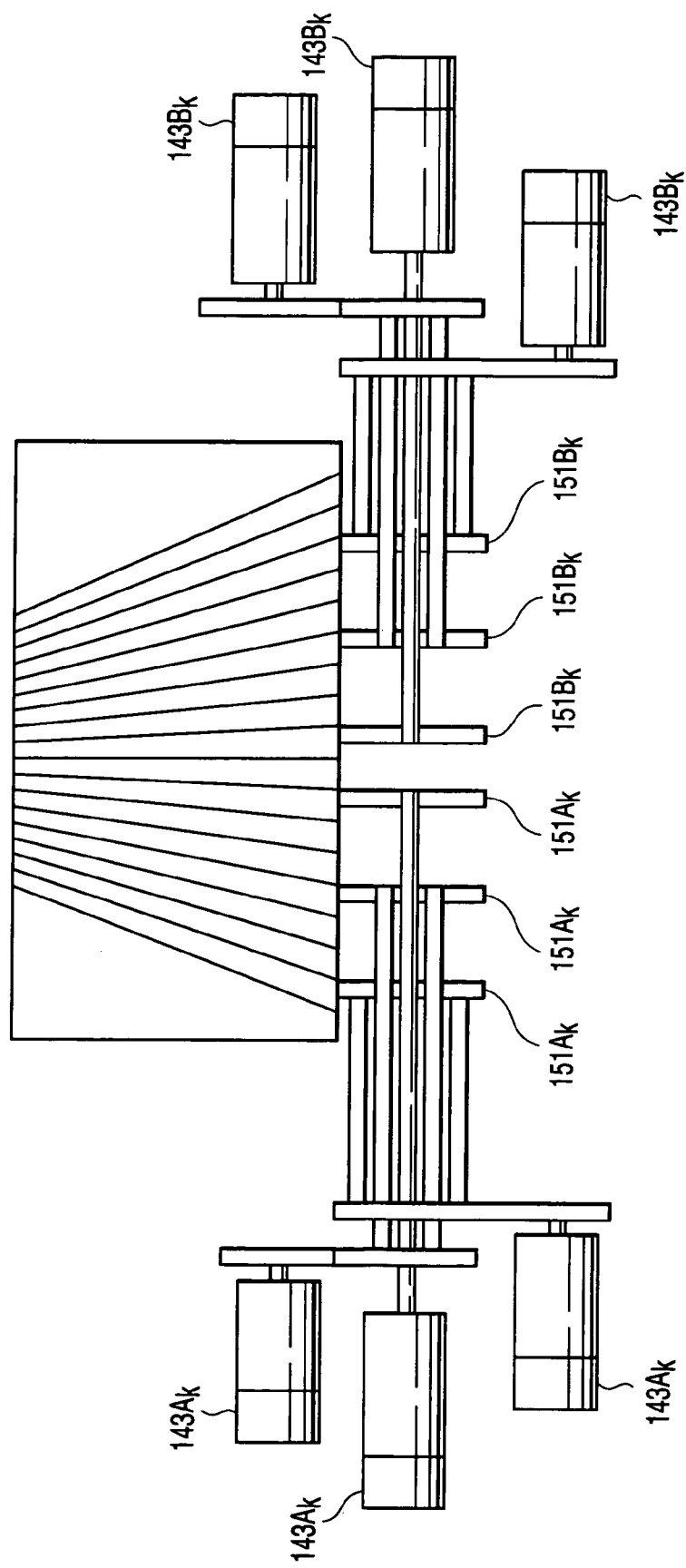
FIG. 10 is a diagram for use in explanation of another example of a diaphragm unit when the diaphragm elements are subdivided.

Subdivision of the second diaphragm member 141A (141B) (increasing the number of the second diaphragm elements) makes it difficult to place the drive units 143Ak and 143Bk (the drive gears 151Ak 151Bk in particular). In such a case, the drive units may be placed in the form of double structure as shown in FIG. 9, allowing the space to accommodate the drive units to be minimized. Further, one axis may be tripled as shown in FIG. 10.

Subdivision of the second diaphragm member results in an increase in the number of cables for connecting the drive units to a power supply. In such a case, the following configuration will allow compact cable accommodation and smooth operation of the diaphragm unit 14 even if the range of rotation is increased.

Figure 11:
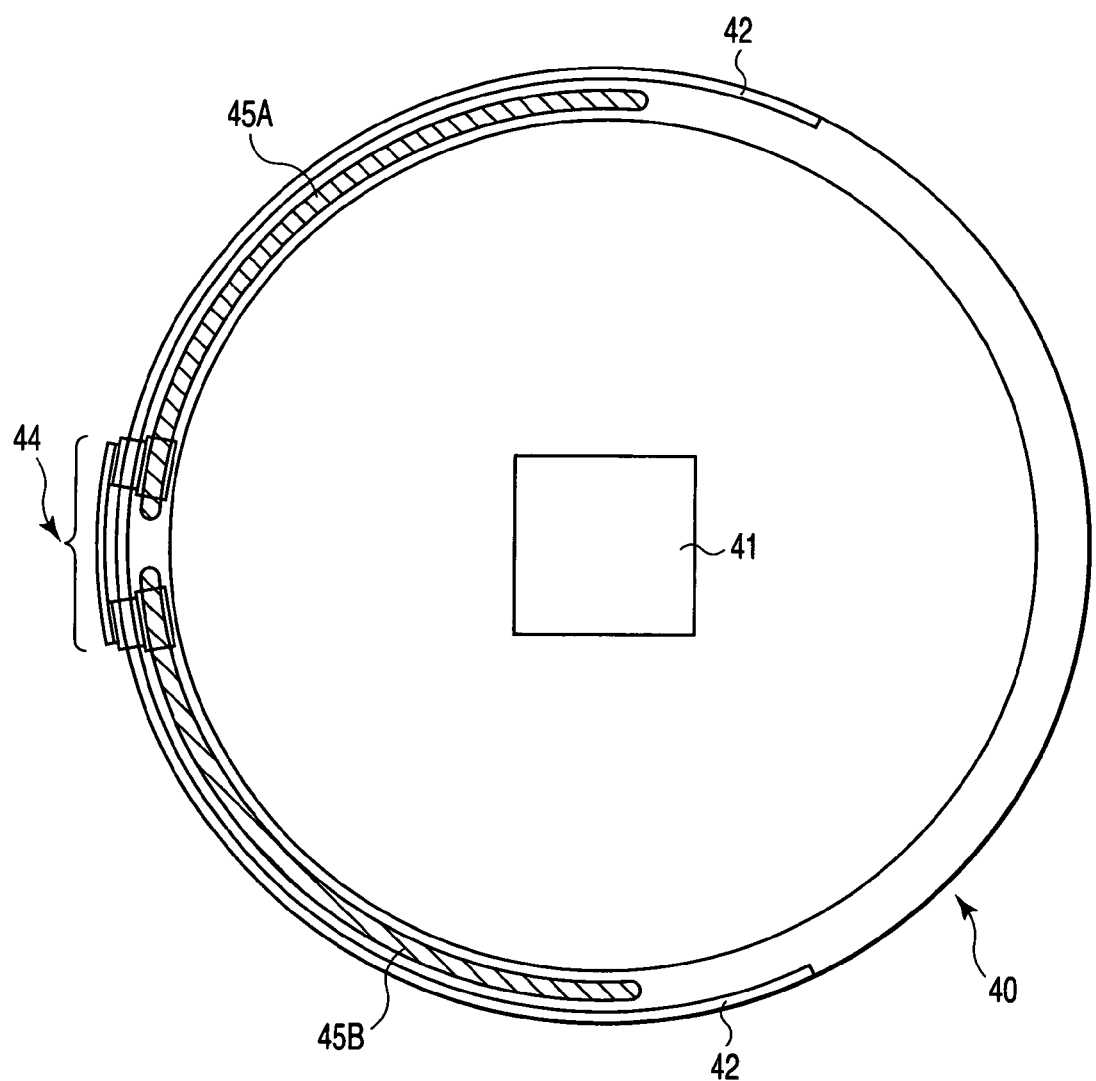
FIG. 11 is a diagram when the diaphragm unit is viewed from the radiation irradiation surface toward the radiation irradiation apparatus.

FIG. 11 is a diagram when the diaphragm unit 14 is viewed from the radiation irradiation surface toward the radiation irradiation apparatus 10. A diaphragm element frame 40 forming a portion of the diaphragm unit 14 is illustrated. The frame 40 is provided at center with an irradiation window 41 which allows radiation from the radiation source S to pass through.

The diaphragm frame 40 is provided with a track rail 42 on its peripheral portion. The rail 42 has an opening corresponding to a central angle which is the same as a given angle within which the diaphragm unit 14 is rotationally moved with respect to the radiation irradiation apparatus 10 in a predetermined range. The rail 42 is spread concentrically with the frame 40 on its peripheral portion with that central angle.

A cable processing mechanism 44 is placed on the rail 42 so as to be movable on the rail. A first cable 45A for the second diaphragm element 141A and a second cable 45B for the second diaphragm element 141Bk are inserted in the cable processing mechanism 44 so as to be movable in the direction of length.

Figure 12:
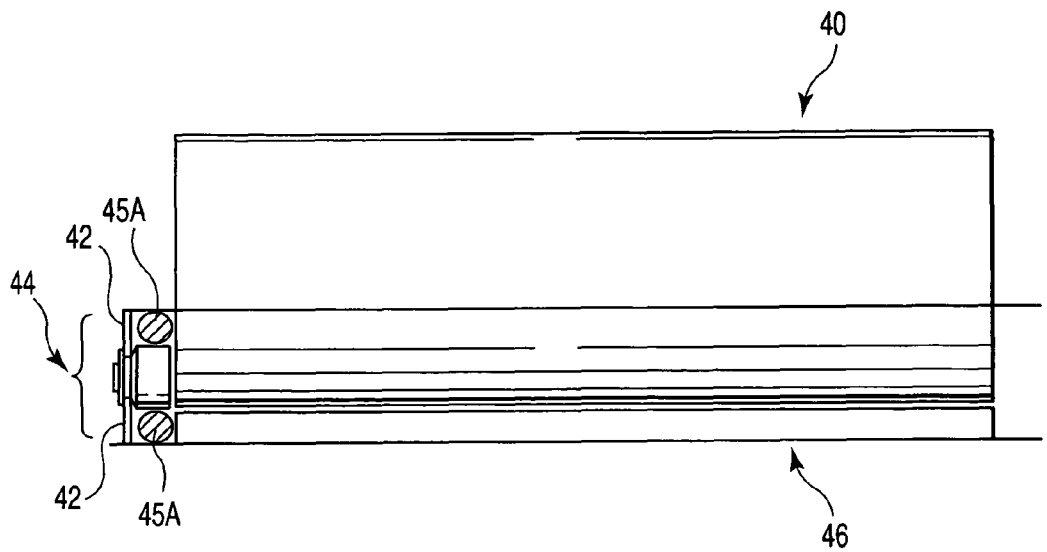
FIG. 12 is a side view of the structure shown in FIG. 11.

FIG. 12 is a side view of the structure shown in FIG. 11. A rotating frame 46 is placed under the diaphragm element frame 40. The diaphragm element frame 40 rotates within a given angle as viewed from the rotating frame 46. The center of rotation coincides with the central axis of the rotating frame 46 and the diaphragm element frame 40. The track rail 42 is provided not only on the diaphragm element frame 40 but also on the rotating frame 46. On the rotating frame 46 the rail 42 is provided in its peripheral portion and its central angle and radius are the same as those of the rail on the diaphragm element frame 46.

In such a configuration, the movement in the direction of length of the first cable 45A causes a rotating roller (not shown) to move, which in turn causes the second cable 45B to move. The first and second cables 45A and 45B are guided by the rail 42 and stored in predetermined positions.

The configuration described above has the following utility.

The radiation diaphragm unit or the radiotherapy apparatus of the present invention is configured to support each leaf-shaped diaphragm element through its elongated hole as well by a shaft-shaped supporting member. Therefore, each diaphragm member is supported in a position close to the center of gravity in addition to support through its peripheral portion. As the result, each diaphragm element made of heavy metal can be supported more stably than before and highly reliable diaphragm operation can be achieved.

The shaft-shaped supporting member to support a diaphragm element in a position close to the center of gravity is coated on top with a wear-resistant material. Thus, abrasion little occurs and stable accuracy can be maintained over a long period of time. Moderate resistance resulting from slide contact allows the looseness (backlash) of each diaphragm element to be minimized.

The main configuration is such that an elongated hole for track is formed in each diaphragm element and a shaft-shaped supporting member is added which is adapted to penetrate through the hole. Therefore, there is no need of providing a supporting part for each diaphragm element and a diaphragm unit can be realized which is smaller and less expensive than before. In addition, the burden of adjustment and repair can be reduced.

Second Embodiment

A second embodiment of the present invention will be described next. In this embodiment, the diaphragm unit 14 is configured such that the surface member 146A (146B) can be rotated about the shaft 145A (145B).

Figure 13:
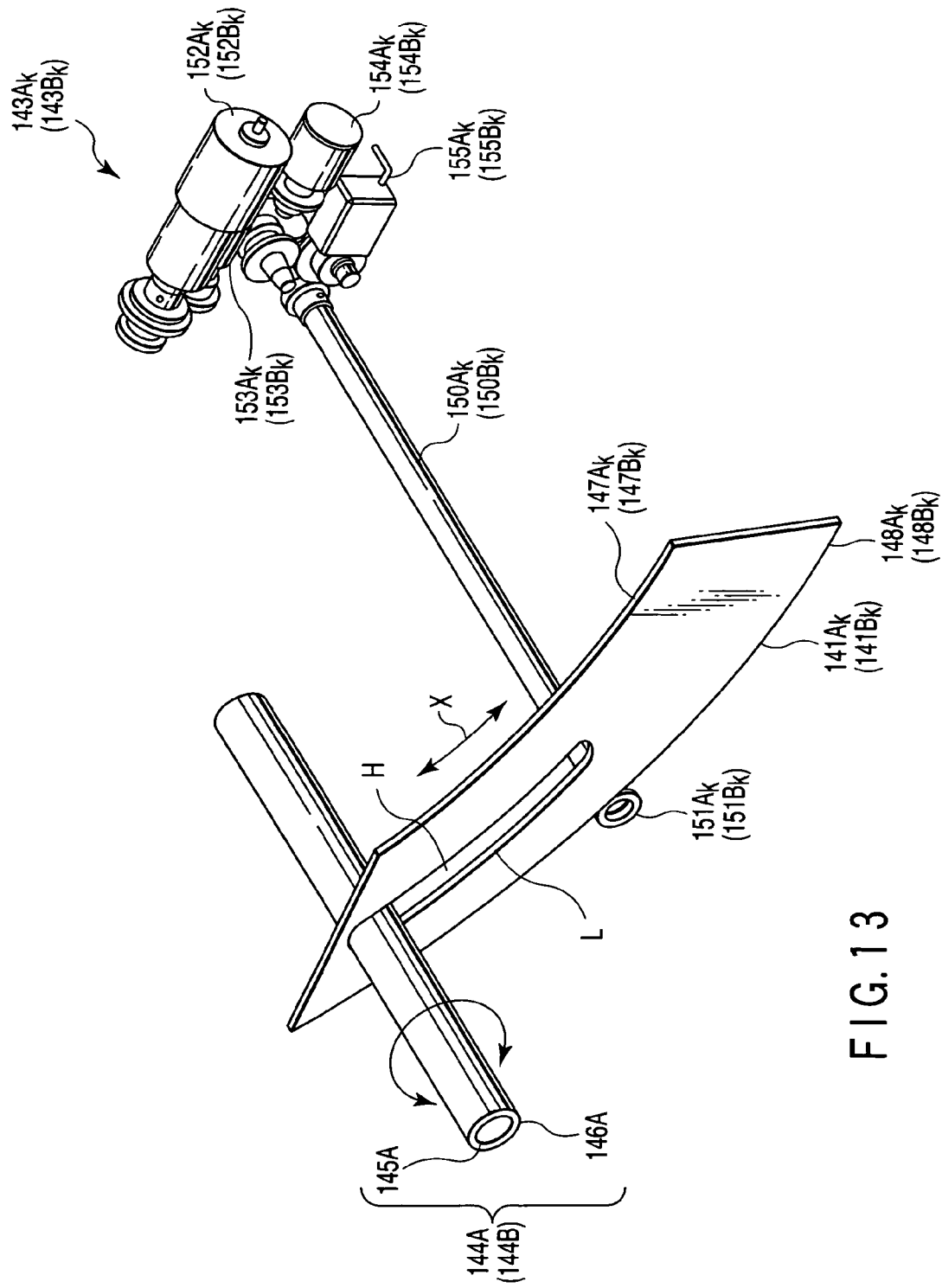
FIG. 13 is a diagram for use in explanation of a surface member and a shaft in the diaphragm unit of a second embodiment of the present invention.

FIG. 13 is a diagram for use in explanation of the surface member 146A (146B) and the shaft 145A (145B) in the diaphragm unit of this embodiment. As shown, the surface member 146A (146B) is adapted to be rotatable about the shaft 145A (145B). The second diaphragm element 141Ak (141Bk) is in contact with the surface member 146A (146B) in the peripheral portion of the elongated hole L and supported at the point of contact by the surface member 146A (146B). Therefore, when the diaphragm element 141Ak (141Bk) moves in the radial direction (the X-direction), the surface member 146A (146B) moves inside the elongated hole L while rotating about the shaft 145A (145B) and changing the point of contact with the diaphragm element.

Such a rotating mechanism using the surface member 146A (146B) and the shaft 145A (145B) can be realized by press fitting a shaft having an inside diameter of, say, a reference value −0.05 into a surface member having a diameter of the reference value +0.05.

Figure 14:
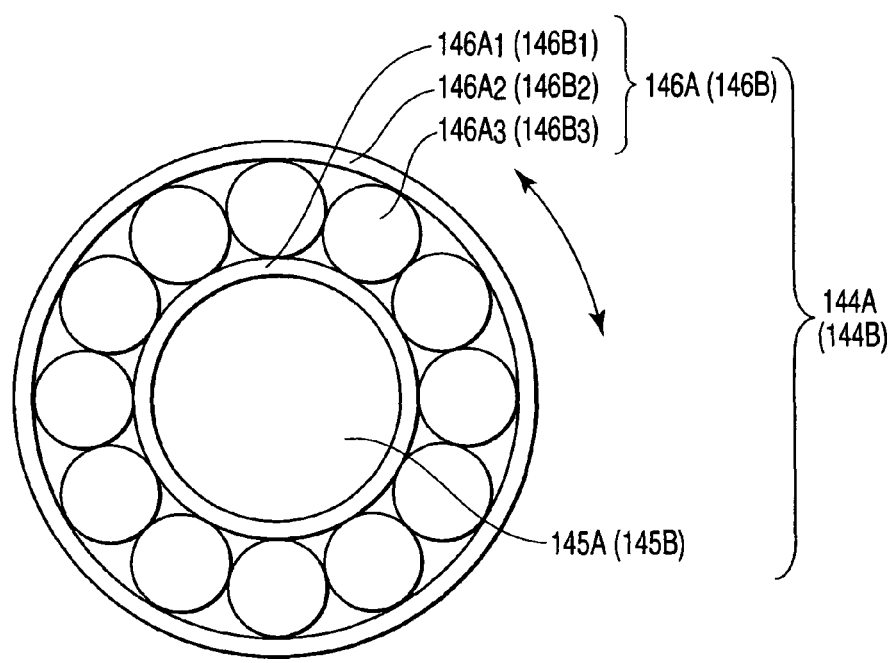
FIG. 14 shows another configuration of the surface member and the shaft in the diaphragm unit of the second embodiment.

FIG. 14 shows another configuration of the surface member 146A (146B) and the shaft 145A (145B) in the diaphragm unit 14 and is a cross sectional view of the surface member and the shaft taken along a direction perpendicular to the direction of the length of the shaft. As shown, the surface member 146A (146B) has an inner ring 146A1 (146B1), an outer ring 146A2 (146B2), and balls 146A3 (146B3). The shaft 145A (145B) is fitted into the inner ring 146A1 (146B1). Even with such a configuration, therefore, when the shaft moves relative to the second diaphragm element 141Ak (141Bk), the surface member can be moved inside the elongated hole L while rotating about the shaft.

According to the diaphragm unit of the second embodiment, when the shaft moves relative to the diaphragm element, the surface member can be rotated about the shaft. It therefore becomes possible to prevent the surface member and the diaphragm element from contacting each other at the same point all the time. As the result, even with long and immoderate use of the apparatus, abrasion little occurs and stable accuracy can be maintained over a long period of time. Moderate resistance resulting from slide contact allows the looseness (backlash) of each diaphragm element 141Ak (141Bk) to be minimized.

The present invention is not limited to the embodiments described above. At the stage of practice of the invention, constituent elements can be embodied in modified forms without departing from the scope thereof. The constituent elements disclosed in the above embodiments can be combined appropriately to form various inventions. For example, some elements may be removed from all the constituent elements shown in the embodiments. In addition, the constituent elements in the different embodiments may be combined appropriately.

What is claimed is:

1. A radiation diaphragm apparatus placed between a radiation source and an object to be examined and adapted to form a radiation field, which is an exposed area of the object to be examined by radiation from the radiation source, the apparatus comprising:
    a plurality of diaphragm elements arranged in a first direction and movable along a second direction different from the first direction, wherein each of the diaphragm elements includes a hole of a predetermined shape formed to penetrate through it in the first direction;
    a first support unit which includes a shaft penetrating through the hole of each of the diaphragm elements and a bush that has a wear-resistant surface and coats the shaft, the bush rotating about an axis of the shaft so that contact points between the wear-resistant surface of the bush and a periphery of the hole vary as each of the diaphragm elements translates in the second direction; and
    a moving unit which moves each of the diaphragm elements along the second direction to form the radiation field.

2. The diaphragm apparatus according to claim 1, wherein the hole of each of the diaphragm elements has a shape corresponding to a shape of the diaphragm element or the locus of movement of the diaphragm element.

3. The diaphragm apparatus according to claim 2, wherein the second direction is the circumferential direction of a circle with center at the radiation source, and each of the diaphragm elements has a shape corresponding to a circular arc of the circle with center at the radiation source.

4. The diaphragm apparatus according to claim 2, wherein the second direction is a direction substantially normal to the irradiation axis of radiation from the radiation source, and each of the diaphragm elements is a polyhedron having a surface substantially normal to the irradiation axis.

5. The diaphragm apparatus according to claim 1, wherein the first support unit defines the limits of movement of the diaphragm elements in the second direction by contacting the diaphragm elements at ends of their respective holes in the second direction.

6. The diaphragm apparatus according to claim 1, further comprising a second support unit configured to support upper and lower peripheries of each of the diaphragm elements.

7. A radiotherapy apparatus, comprising:
    a radiation source to irradiate an object to be examined with radiation;
    a radiation diaphragm unit placed between the radiation source and an object to be examined and adapted to form a radiation field, which is an exposed area of the object to be examined to radiation from the radiation source, which comprises a plurality of diaphragm elements arranged in a first direction and movable along a second direction different from the first direction, wherein each of the diaphragm elements includes a hole of a predetermined shape formed to penetrate through it in the first direction, and a first support unit which includes a shaft penetrating through the hole of each of the diaphragm elements, and a bush that has a wear-resistant surface and coats the shaft, the bush rotating about an axis of the shaft so that contact points between the wear-resistant surface of the bush and a periphery of the hole vary as each of the diaphragm elements translates in the second direction;
    a moving unit which moves each of the diaphragm elements along the second direction to form the radiation field; and
    a control unit which controls the moving unit.

8. The radiotherapy apparatus according to claim 7, wherein the hole of each of the diaphragm elements has a shape corresponding to a shape of the diaphragm element or the locus of the diaphragm element movement.

9. The radiotherapy apparatus according to claim 8, wherein the second direction is the circumferential direction of a circle with center at the radiation source, and each of the diaphragm elements has a shape corresponding to a circular arc of the circle with center at the radiation source.

10. The radiotherapy apparatus according to claim 8, wherein the second direction is a direction substantially normal to the irradiation axis of radiation from the radiation source, and each of the diaphragm elements is a polyhedron having a surface substantially normal to the irradiation axis.

11. The radiotherapy apparatus according to claim 8, wherein the supporting unit defines the limits of movement of the diaphragm elements in the second direction by contacting the diaphragm elements at ends of their respective holes in the second direction.

12. The radiotherapy apparatus according to claim 7, further comprising a second support unit configured to support upper and lower peripheries of each of the diaphragm elements.

* * * * *